United States Patent [19]

Vanlerberghe et al.

[11] 4,247,411

[45] Jan. 27, 1981

[54] STORAGE STABILITY OF AQUEOUS DISPERSIONS OF SPHERULES

[75] Inventors: Guy Vanlerberghe, Commune de Villevaude; Rose-Marie J. Handjani, Paris, both of France

[73] Assignee: L'Oreal, Paris, France

[21] Appl. No.: 8,115

[22] Filed: Jan. 31, 1979

[30] Foreign Application Priority Data

Feb. 2, 1978 [FR] France ............... 78 02927

[51] Int. Cl.³ ............... B01J 13/02; A01N 25/28; A61K 9/50; A61K 9/64
[52] U.S. Cl. ............... 252/316; 424/36; 424/59; 424/62; 424/65; 424/85; 424/94; 424/280; 424/317
[58] Field of Search ............... 252/316; 424/36; 427/398 C, 398.4

[56] References Cited

U.S. PATENT DOCUMENTS

| | | | |
|---|---|---|---|
| 1,959,930 | 5/1934 | Schmidt et al. | 252/356 X |
| 3,041,289 | 6/1962 | Katchen et al. | 252/316 |
| 3,173,878 | 3/1965 | Reyes | 252/316 |
| 3,336,155 | 8/1967 | Rowe | 252/316 X |
| 3,630,920 | 12/1971 | Freifeld et al. | 252/90 |
| 3,932,657 | 1/1976 | Rahman | 424/365 X |
| 3,957,971 | 5/1976 | Oleniacz | 424/365 X |
| 4,016,100 | 4/1977 | Suzuki et al. | 252/316 |

FOREIGN PATENT DOCUMENTS

| | | | |
|---|---|---|---|
| 2249552 | 5/1973 | Fed. Rep. of Germany | 252/316 |
| 1477048 | 3/1967 | France | 252/351 |
| 2298318 | 8/1976 | France | 252/316 |

OTHER PUBLICATIONS

Chem. Abstracts, vol. 85, No. 2, p. 258, Jul. 26, 1976.

*Primary Examiner*—Richard D. Lovering
*Attorney, Agent, or Firm*—Cushman, Darby & Cushman

[57] ABSTRACT

Aqueous dispersions of spherules in the form of organized molecular layers of lipids, between which is encapsulated an aqueous phase containing at least one active substance are rendered more storage-stable by lyophilization. They can readily be reconstituted by re-hydration.

14 Claims, No Drawings

STORAGE STABILITY OF AQUEOUS DISPERSIONS OF SPHERULES

DESCRIPTION

It is known that certain lipids possess the property that, in the presence of an aqueous phase, they form mesomorphic phases in which the state of organisation is intermediate between the crystalline state and the liquid state. It is known that some of these lipids can swell in aqueous solution to form small spheres dispersed in the aqueous medium, these small spheres consisting of essentially concentric sheets, the sheets being in the form of bimolecular or multimolecular layers. Small spheres of this type (spherules), which are generally referred to as liposomes, can be used for enclosing aqueous solutions of active substances, the said substances being in the aqueous compartments between the lipid layers and thus being protected against the exterior.

It has already been proposed to obtain liposomes from ionic lipids, these liposomes corresponding to the general formula: X—Y in which X is a polar hydrophilic group and Y is a non-polar hydrophobic group; for example, French Pat. No. 2,221,122 describes such liposomes having diameters less than 1,000 Å, and French Pat. No. 75/20456 describes such liposomes having diameters from 1,000 to 50,000 Å. Further, French Pat. No. 2,315,991 describes liposomes which have a diameter from 100 to 50,000 Å and are obtained from a water-dispersible lipid having the general formula:

$$X-Y$$

in which formula X represents a non-ionic hydrophilic group and Y represents a lipophilic group. Thus, ionic and non-ionic liposome dispersions of various sizes are known; British Application No. 44,492/78 describes dispersions containing several types of liposomes, each type containing different active substances.

In practice, the value of compositions containing ionic or non-ionic liposomes is limited by two essential characteristics of these liposomes, namely their stability and their impermeability. It is necessary to ensure that the liposomes in question have a sufficiently high stability, so that these liposomes remain in the form of small spheres for a sufficiently long time to enable the compositions to be used before the small spheres have coalesced. In fact, the thermodynamically stable state of organisation of hydrated lipids is that of the lamellar phase having a sheet-like structure; there is therefore a tendency for the small spheres to coalesce and this tendency depends principally on the size of the liposomes and on the nature of the lipids. Furthermore, it is necessary to be able to have available liposomes which keep encapsulated the active substances enclosed between the lipid layers, and, in this respect, it has moreover been found that liposomes having relatively large sizes, for example from 1,000 to 50,000 Å, are of greater value than liposomes having relatively small sizes, for example from 100 to 1,000 Å, by virtue of the fact that the permeability of these liposomes decreases as the mean diameter of the liposomes increases. It is therefore very important from a practical point of view to find a way of improving the stability and impermeability of such liposomes so that they can be used satisfactorily a long time after they have been manufactured.

It has been found, according to the present invention, very surprisingly, that when the compositions containing liposomes are lyophilised, they can subsequently be rehydrated to substantially their former state without the lyophilisation modifying the structure and the size of the spherules. This observation is particularly surprising when it is remembered that liposomes have an entirely lipidic structure organised around the water and that, in contrast to cells of the conventional type, the lyophilisation of which is known, liposomes do not benefit from stabilisation factors due to the presence of polymers such as proteins. Moreover, the formation of the liposomes depends on the state of arrangement of the lipidic chains, that is to say it is directly related to the temperature, it only being possible for saturated long-chain lipids to give liposomes above a certain temperature, this essentially corresponding to the melting point of the paraffin chains in the lipids in question. The lyophilisation process does, of course, use low temperatures and, as a result, one would have expected this lyophilisation to destroy the structure of the liposomes. However, in contrast to all such logical deductions, the passage of liposomes through low temperatures and the removal of water do not destroy the structure of the liposomes, with the result that the liposome lyophilisates can be rehydrated and can reproduce, on rehydration, aqueous dispersions which are substantially identical to the initial dispersions i.e. prior to lyophilisation.

It is clear that this invention makes it possible to improve considerably the possible practical uses of liposomes, because, by means of lyophilisation, any conversion of the liposomes, that is to say any coalescence or migration, through permeability, of the active substances enclosed in the liposomes, can be avoided throughout the time the liposomes are kept in the lyophilised state. In fact, it has been possible to observe that this lyophilisation process permits the production of liposomes in which the amount of substance encapsulated is not modified during evaporation of the water. Moreover, after rehydration of the lyophilisate, it is observed that the size of the liposomes is the same as that prior to lyophilisation. This invention therefore makes it possible to envisage the preparation, for immediate use, of dispersions of liposomes having sizes which are very highly unstable, because they can be lyophilised sufficiently rapidly; after they have been prepared, to enable them to be kept for any length of time in the lyophilised state and to subsequently regenerate them by rehydration at the desired moment. Moreover, the liposome lyophilisates according to the present invention possesses the general advantages of lyophilised products from the point of view of protection against bacterial contamination and of oxidation, in particular.

The present invention consequently provides a process for improving the storage stability of an aqueous dispersion of small spheres or spherules (liposomes) which consist of organised molecular layers between which is encapsulated an aqueous phase containing at least one active substance, these layers consisting of at least one lipid having the general formula:

$$X-Y$$

in which formula Y represents a lipophilic group and X represents an ionic or non-ionic hydrophilic group, the diameter of the spherules being from about 100 to 50,000 Å, which comprises after having prepared the aqueous dispersion of liposomes in known manner, lyophilising the said dispersion, in order to obtain a paste or a solid. It is intended that the lyophilisate is rehydrated, shortly before the composition is to be used, in order to regenerate the initial composition.

In a preferred method of carrying out the process according to the invention, fillers are introduced into the liposome composition, these fillers being intended to prevent the solidification or caking of the products obtained by lyophilisation; the fillers are advantageously inorganic salts, colloidal silica, starches or aluminosilicates such as bentonites. The lyophilisation is carried out by lowering the temperature of the liposome composition to, say, below −30° C., the composition suitably being arranged as a thin layer and by evaporating it at a temperature of, say, 15° to 60° C. under a very low pressure; the evaporation pressure is of the order of 0.01 millibar, the temperature of the condenser being about −70° C. and the evaporation being continued for, say, 12 hours.

The present invention also provides the lyophilised liposome composition produced in the process.

The lipids constituting the liposomes can be either ionic compounds or non-ionic compounds; the liposomes in the composition may be of at least two types and the active substances enclosed in the liposomes of each type can be different. Y generally represents a lipophilic chain containing from 12 to 30 carbon atoms, advantageously lauryl, tetradecyl, hexadecyl, oleyl, isostearyl, lanolyl or alkylphenyl chains, X is advantageously a non-ionic hydrophilic group such as polyoxyethylenated or polyglycerolated groups and polyol esters which may or may not be oxyethylenated. X can also advantageously be an ionic hydrophilic group such as one formed by an amphoteric compound containing two lipophilic chains with an association of two ions of opposite sign.

When the lipids are non-ionic compounds, they are advantageously selected from:
a linear or branched polyglycerol ether of the respective formulae:

or

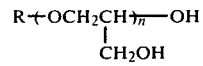

n being an integer from 1 to 6 and R being a saturated or unsaturated, linear or branched, aliphatic chain containing from 12 to 30 carbon atoms, a hydrocarbon radical of a lanoline alcohol or a 2-hydroxyalkyl radical of a long-chain α-diol
a polyoxyethylenated fatty alcohol;
a polyol ester which may or may not be oxyethylenated, for example a polyoxyethylenated sorbitol ester;
a glycolipid of natural or synthetic origin, for example a cerebroside.

In the composition which is subjected to lyophilisation, the aqueous phase encapsulated in the liposomes is an aqueous solution of one or more active substances; the continuous phase which surrounds the liposomes is an aqueous phase which is isotonic relative to the encapsulated phase of the dispersion; the ratio of the weight of the liposomes to the weight of the continuous phase of the dispersion is generally from 0.01 to 0.5.

When the liposomes are obtained from non-ionic lipidic compounds, the compositions subjected to lyophilisation can comprise various additives for the purpose of modifying the permeability or the surface charge of the liposomes. In this respect, there can be mentioned the optional addition of long-chain alcohols and diols, sterols, for example cholesterol, long-chain amines and their quaternary ammonium derivatives, dihydroxyalkylamines, polyoxyethylenated fatty amines, esters of long-chain aminoalcohols and their salts and quaternary ammonium derivatives, phosphoric acid esters of fatty alcohols, for example sodium dicetyl-phosphate, alkyl-sulphates, for example sodium cetyl-sulphate, and certain polymers such as polypeptides and proteins.

The composition subjected to lyophilisation can comprise liposomes containing active substances of all kinds, in particular substances of pharmaceutical or nutritional value or substances having a cosmetic action. Suitable cosmetic substances include products intended for skin care and hair care, for example humectants such as glycerol, sorbitol, pentaerythritol, inositol and pyrrolidonecarboxylic acid and its salts; artificial tanning agents such as dihydroxyacetone, erythrulose, glyceraldehyde and γ-dialdehydes such as tartaric aldehyde, (optionally in association with colourants); water-soluble anti-sunburn agents; antiperspirants, deodorants, astringents and freshening, toning, cicatrisant, keratolytic and depilatory products; perfumed water; extracts of animal or plant tissues, such as proteins, polysaccharides and amniotic liquid; water-soluble hair dyes, anti-dandruff agents, anti-seborrhoea agents, oxidising agents (bleaching agents) such as hydrogen peroxide, and reducing agents such as thioglycolic acid and its salts. Pharmaceutically active substances which may be mentioned include: vitamins, hormones, enzymes (for example superoxide dismutase), vaccines, anti-inflammatory agents (for example hydrocortisone), antibiotics and bactericides.

The following Examples further illustrate the present invention.

EXAMPLE 1

320 mg of the product of the general formula:

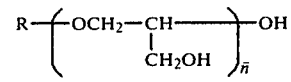

R being the alkyl radical of the alcohols of hydrogenated lanoline and $\bar{n}$ having a mean statistical value of 3, and 80 mg of cholesterol are dissolved, in a 100 ml round-bottomed flask, in 5 ml of a 2:1 mixture of chloroform and methanol. The solvent is evaporated off on a rotary evaporator and the final traces of solvent are then removed by subjecting the product for 1 hour to the reduced pressure provided by a vane pump.

At 40° C., the lipid film obtained is brought into contact with 10 ml of a 8% strength aqueous solution of the triethanolamine salt of urocanic acid. The round-bottomed flask is then placed on a shaker and shaken vigorously for 2 hours at 40° C.; it is then cooled gradually until it returns to ambient temperature. The dispersion obtained is fluid. The size of the liposomes is less than or equal to one micron.

The round-bottomed flask is immersed in liquid nitrogen and rotated, in order to freeze the product on the walls of the round-bottomed flask, and it is then placed in a lyophiliser for 12 hours. This yields a pasty product which is kept for several days.

By adding at least 3.5 ml of water to the lyophilised product kept in this way, a dispersion of small spheres having a diameter which is less than or equal to one micron is again obtained.

EXAMPLE 2

190 mg of the product of the general formula:

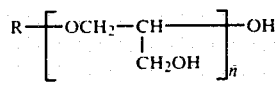

in which: R is the hexadecyl radical and $\overline{n}$ has a mean statistical value of 3, 190 mg of cholesterol and 20 mg of sodium dicetyl-phosphate are intimately mixed, using a spatula, in the bottom of a 30 ml test tube. Mixing is carried out at a temperature of 90° C. which is brought down to 70° C. by means of a water bath.

The mixture obtained is then brought into contact with 2.5 ml of a 2% strength aqueous solution (pH 7) of the sodium salt of L-pyrrolidonecarboxylic acid. The resulting mixture is homogenised, using a spatula, until a highly hydrated lamellar phase is obtained. 7.5 ml of the 2% strength aqueous solution (pH 7) of the sodium salt of L-pyrrolidonecarboxylic acid are added. The head of an ultra-disperser sold under the tradename "ILA" is immersed deep in the dispersion. Dispersion is carried out, the speed of rotation gradually being increased up to the maximum speed, which is maintained for about 30 minutes. The temperature of the water bath is allowed to return gradually to ambient temperature. The dispersion obtained is fluid. The size of the liposomes is of the order of one micron.

The dispersion is transferred into a 100 ml round-bottomed flask which is immersed in liquid nitrogen and rotated, in order to freeze the product on the walls of the round-bottomed flask, and is then placed in a lyophiliser for 12 hours. This yields a pasty product which is white in colour and can be kept.

By adding more than 3.5 ml of water to the lyophilised product, a dispersion of individualised small spheres having a mean size of the order of one micron is obtained.

The liposome dispersion can be subjected to ultrasonics prior to lyophilisation; the size of the spheres is then very small (diameter: 500–1,000 Å). After lyophilisation and rehydration of the lyophilisate, a dispersion of liposomes of the same diameter is obtained.

EXAMPLE 3

75 mg of the product of the general formula:

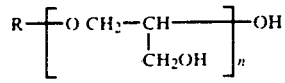

R being the hexadecyl radical and n being equal to 2, 20 mg of cholesterol and 5 mg of dicetyl phosphate are intimately mixed, using a spatula, in the bottom of a 30 ml test tube. Mixing is carried out at a temperature of 70° C. obtained by means of a water bath.

This mixture is brought into contact with 2.5 ml of a 5% strength aqueous solution of sodium chloride. The resulting mixture is homogenised, using a spatula, until a highly hydrated lamellar phase is obtained. 7.5 ml of the 5% strength aqueous solution of sodium chloride are added. The head of an "ILA" ultra-disperser is immersed deep in the dispersion. Dispersion is carried out, the speed of rotation of the head gradually being increased up to the maximum speed, which is maintained for about 30 minutes. The temperature of the water bath is allowed to return gradually to ambient temperature. The dispersion obtained is fluid. The size of the liposomes is of the order of one micron.

The dispersion is transferred into a 100 ml round-bottomed flask which is immersed in liquid nitrogen and rotated, in order to freeze the product on the walls of the round-bottomed flask. The round-bottomed flask is left in a lyophiliser for 12 hours. This yields a powdery product which is white and can be kept.

By adding at least 1 ml of water to the product which has been kept, a dispersion of individualised small spheres having a mean size of the order of one micron is obtained.

The initial dispersion can also be subjected to ultrasonics prior to lyophilisation, in order to reduce the size of the liposomes in the dispersion.

EXAMPLE 4

128 mg of hydrogenated egg lecithin, 15 mg of cholesterol and 7 mg of dicetyl phosphate are dissolved, in a 100 ml round-bottomed flask, in 5 ml of a 2:1 mixture of chloroform and methanol. The solvent is evaporated off on a rotary evaporator and the final traces of solvent are then removed by subjecting the product for 1 hour to the reduced pressure provided by a vane pump.

The lipid film obtained is brought into contact with 4 ml of a 0.3 M aqueous solution of ascorbic acid. The experiment is carried out at a temperature of 40° C. The round-bottomed flask, placed on a shaker, is shaken vigorously for 2 hours at 40° C. and then cooled gradually until it returns to ambient temperature. The dispersion obtained is fluid. The size of the liposomes is less than or equal to one micron.

The round-bottomed flask is immersed in liquid nitrogen and rotated, in order to freeze the product on the walls of the flask, and it is then placed in a lyophiliser for 12 hours. This yields a pasty product which is white and can be kept.

By adding more than 1.5 ml of water to the product which has been kept, a dispersion of individualised liposomes having sizes which are less than or equal to one micron is obtained.

The initial dispersion can also be subjected to ultrasonics prior to lyophilisation, in order to reduce the size of the liposomes.

EXAMPLE 5

300 mg of egg lecithin, 80 mg of cholesterol and 20 mg of dicetyl phosphate are intimately mixed, using a spatula, in the bottom of a 30 ml test tube. Mixing is carried out at a temperature of 60° C. which is then brought down to 40° C. by means of a water bath.

The mixture obtained is then brought into contact with 2.5 ml of a 2.5% strength aqueous solution (pH=7) of the sodium salt of lactic acid. The resulting mixture is homogenised, using a spatula, until a highly hydrated lamellar phase is obtained. 7.5 ml of the 2.5% strength aqueous solution of the sodium salt of lactic acid are then added. The head of an "ILA" ultra-disperser is immersed deep in the dispersion. Dispersion is carried out, the speed of rotation of the head gradually being increased up to the maximum speed, which is maintained for about 30 minutes. The temperature of the water bath is allowed to return gradually to ambient temperature. The dispersion obtained is fluid. The size of the liposomes is greater than one micron. The dispersion can be subjected to ultra-sonics under nitrogen; the size of the liposomes then becomes very much less than one micron (250–1,000 Å).

The dispersion obtained is transferred into a 100 ml round-bottomed flask which is immersed in liquid nitrogen and rotated, in order to freeze the product on the walls of the round-bottomed flask. The round-bottomed flask is then left in a lyophiliser for 12 hours. This yields a flaky product which is brown in colour and can be kept.

By rehydrating the product, which has been kept, with at least 3.5 ml of water, individualised liposomes having a size of less than (250–1,000 A) or more than one micron are reproduced, depending on whether or not the dispersion has been subjected to ultra-sonics prior to lyophilisation.

EXAMPLE 6

300 mg of egg lecithin, 80 mg of cholesterol and 20 mg of sodium dicetyl-phosphate are intimately mixed, using a spatula, in the bottom of a 30 ml test tube. Mixing is carried out at a temperature of 60° C. which is then brought down to 40° C. by means of a water bath.

The mixture obtained is then brought into contact with 2.5 ml of a 1°/oo strength aqueous solution of the enzyme superoxide dismutase. The resulting mixture is homogenised, using a spatula, until a highly hydrated lamellar phase is obtained. 7.5 ml of the 1°/oo strength aqueous solution of the enzyme superoxide dismutase are added. The head of an "ILA" ultra-disperser is immersed deep in the dispersion. Dispersion is carried out, the speed of rotation of the head gradually being increased up to the maximum speed, which is maintained for about 30 minutes. The temperature of the water bath is allowed to return gradually to ambient temperature. The dispersion obtained is fluid. The size of the liposomes is greater than one micron. The dispersion can be subjected to ultra-sonics under nitrogen; the size of the liposomes then becomes very much less than one micron (250–1,000 A).

The dispersion obtained is transferred into a 100 ml round-bottomed flask and 300 mg of aluminosilicate are introduced into the round-bottomed flask which is placed on a shaker for about 30 minutes. This round-bottomed flask is immersed in liquid nitrogen and rotated, in order to freeze the product on the walls of the flask. The round-bottomed flask is then left in a lyophiliser for 12 hours. This yields a white powdery product which can be kept.

By rehydrating the product, which has been kept, with at least 3.5 ml of water, individualised liposomes having a size which is less than (250–1,000 A) or greater than one micron are reproduced, depending on whether or not the dispersion has been subjected to ultra-sonics prior to lyophilisation.

EXAMPLE 7

320 mg of the product of the general formula

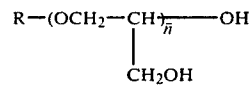

R being the alkyl radical of the alcohols of hydrogenated lanoline and $\bar{n}$ having a mean statistical value of 3, and 80 mg of cholesterol are dissolved, in a 100 ml round-bottomed flask, in 5 ml of a 2:1 mixture of chloroform and methanol. The solvent is evaporated off on a rotary evaporator and the final traces of solvent are then removed by subjecting the product for 1 hour to the reduced pressure provided by a vane pump.

At a temperature of 40° C., the lipid film obtained is brought into contact with 10 ml of a 3% strength aqueous solution of glycerol.

The round-bottomed flask is then placed on a shaker and shaken vigorously for 2 hours at 40° C.; it is then cooled gradually until it returns to ambient temperature. The dispersion obtained is fluid. The size of the liposomes is less than or equal to one micron.

500 mg of aluminosilicate are introduced into the round-bottomed flask which is then placed on the shaker again for about 30 minutes.

The round-bottomed flask is immersed in liquid nitrogen and rotated, in order to freeze the product on the walls of the round-bottomed flask, and it is then placed in a lyophiliser for 12 hours. This yields a white powdery product which can be kept.

By adding at least 3.5 ml of water to the lyophilised product kept in this way, a dispersion of small spheres having a diameter which is less than or equal to one micron is again obtained.

EXAMPLE 8

180 mg of the product of the general formula

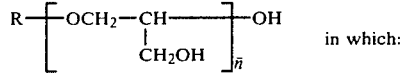 in which:

R is the hexadecyl radical and $\bar{n}$ has a mean statistical value of 3, 180 mg of cholesterol and 40 mg of sodium dicetyl-phosphate are intimately mixed, using a spatula, in the bottom of a 30 ml test tube. Mixing is carried out at a temperature of 90° C. which is then brought down to 50° C. by means of a water bath.

The mixture obtained is then brought into contact with 2.5 ml of a 5% strength aqueous solution of immunoglobulins Ig A. The resulting mixture is homogenised, using a spatula, until a highly hydrated lamellar phase is obtained. 7.5 ml of a 9°/oo strength aqueous solution of sodium chloride are added. The head of an ultradisperser sold under the name "ILA" is immersed deep in the dispersion. Dispersion is carried out, the speed of rotation gradually being increased up to the maximum speed, which is maintained for about 30 minutes. The temperature of the water bath is allowed to return gradually to ambient temperature. The dispersion obtained is fluid. The size of the liposomes is greater than or equal to one micron.

The round-bottomed flask is immersed in liquid nitrogen and rotated, in order to freeze the product on the walls of the round-bottomed flask, and it is then placed in a lyophiliser for 12 hours. This yields a white powdery product.

By adding more than 3.5 ml of water to the lyophilised product, a dispersion of individualised small spheres having a mean size which is greater than or equal to one micron is obtained.

We claim:

1. A process for preserving an aqueous dispersion of spherules in the form of organized molecular layers between which is encapsulated an aqueous phase containing at least one active substance, these layers consisting of at least one lipid having the formula X—Y wherein Y represents a lipophilic group and X represents an ionic or non-ionic group, the diameter of the spherules being from 100 to 50,000 Å, which comprises lowering the temperature of the dispersion to below about $-30°$ C. and evaporating it at a temperature from about 15° to about 60° C. under reduced pressure thereby producing a lyophilized product as a paste or a solid.

2. The process of claim 1 wherein the dispersion contains one or more fillers adapted to impede agglomeration of the lyophilized product.

3. The process of claim 2 wherein the filter is an inorganic salt, colloidal silica, starch or an alumino silicate.

4. The process of claim 1 wherein the lipid is selected from the group consisting of ionic compound and non-ionic compound.

5. The process of claim 1 wherein the lipids are of at least two types, the active substances enclosed in the lipids of each type being different.

6. The process of claim 1 wherein Y represents a lipophilic chain containing from 12 to 30 carbon atoms.

7. The process of claim 6 wherein Y is selected from the group consisting of lauryl, tetradecyl, hexadecyl, oleyl, isostearyl, lanolyl and alkylphenyl chains.

8. The process of claim 1 wherein X represents a non-ionic hydrophilic group selected from the group consisting of polyoxyethylenated group, polyglycerolated group and oxyethylenated polyol esters.

9. The process of claim 1 wherein X is an ionic hydrophilic group formed from an amphoteric compound containing two lipophilic chains with an association of two organic ions of opposite sign.

10. The process of claim 1 wherein the lipid is selected from the group consisting of (i) linear and branched polyglycol esters of the formulae:

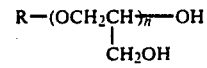

wherein n is an integer from 1 to 6 and R is selected from the group consisting of saturated and unsaturated, linear and branched, aliphatic chains containing from 12 to 30 carbon atoms; hydrocarbon radicals of lanolin alcohols, and 2-hydroxyalkyl radicals of long-chain α-diols, (ii) polyoxyethylenated fatty alcohols,
(iii) polyol esters oxyethylenated or not and
(iv) glycolipids of natural or synthetic origin.

11. The process of claim 1 wherein the dispersion contains one or more long-chain alcohols or diols, sterols, long-chain amines or their quaternary derivatives, dihydroxyalkylamines, polyoxyethylenated fatty amines, esters of long-chain aminoalcohols or their salts or quaternary ammonium derivatives, phosphoric acid esters of fatty alcohols, alkyl sulfates, polypeptides and proteins.

12. The process of claim 1 wherein the active substance is a humectant, an artificial tanning agent, alone or with a colorant, a water-soluble anti-sunburn agent, an antiperspirant, a deodorant, an astringent, a freshening agent, a toning agent, a cicatrisant, a keratolytic or depilatory product, a perfumed water, an extract of animal or plant tissue, a water-soluble hair dye, an anti-dandruff agent, an anti-seborrhea agent, a cosmetic oxidizing agent or a cosmetic reducing agent.

13. The process of claim 1 wherein the active substance is a vitamin, nutritional substance, hormone, enzyme, vaccine, anti-inflammatory agent, antibiotic or bactericide.

14. A process for preparing an aqueous dispersion of spherules in the form of organized molecular layers between which is encapsulated an aqueous phase containing at least one active substance, these layers consisting of at least one lipid having the formula X—Y wherein Y represents a lipophilic group and X represents an ionic or non-ionic group, the diameter of the spherules being from 100 to 50,000 Å, which comprises lowering the temperature of the dispersion to below about $-30°$ C., evaporating it at a temperature from about 15° to about 60° C. under reduced pressure thereby producing a lyophilized product as a paste or a solid and hydrating said lyophilized product.

* * * * *

UNITED STATES PATENT AND TRADEMARK OFFICE
CERTIFICATE OF CORRECTION

PATENT NO. : 4,247,411

DATED : January 27, 1981

INVENTOR(S) : Guy VANLERBERGHE

It is certified that error appears in the above-identified patent and that said Letters Patent is hereby corrected as shown below:

IN THE CLAIMS:

Claim 3, first line, change "filter" to --filler--

Signed and Sealed this

Fifteenth Day of May, 1990

Attest:

HARRY F. MANBECK, JR.

Attesting Officer

Commissioner of Patents and Trademarks